United States Patent [19]

Shepard et al.

[11] Patent Number: 5,710,255
[45] Date of Patent: Jan. 20, 1998

[54] CHARACTERIZATION OF A NOVEL ANTI-P110$^{RB}$ MONOCLONAL ANTIBODY

[75] Inventors: H. Michael Shepard, Carlsbad; Shu Fen Wen, San Diego, both of Calif.

[73] Assignee: Canji, Inc., San Diego, Calif.

[21] Appl. No.: 204,329

[22] PCT Filed: Jul. 14, 1992

[86] PCT No.: PCT/US92/05866

§ 371 Date: Aug. 15, 1994

§ 102(e) Date: Aug. 15, 1994

[87] PCT Pub. No.: WO94/01467

PCT Pub. Date: Jan. 20, 1994

[51] Int. Cl.$^6$ .................... C07K 16/00; C12P 21/08; C12N 5/00; A61K 39/395
[52] U.S. Cl. .................... 530/388.8; 435/330; 435/331; 435/344; 424/138.1
[58] Field of Search .............. 424/138.1, 139.1, 424/141.1, 155.1, 156.1; 435/240.27, 7.23; 530/387.7, 387.9, 388.1, 388.15, 388.8

[56] References Cited

U.S. PATENT DOCUMENTS 4,942,123   7/1990   Lee et al. .................... 435/6

FOREIGN PATENT DOCUMENTS

A-0390530   3/1990   European Pat. Off. .
WO-A-9012807   1/1990   WIPO .

OTHER PUBLICATIONS

"Monoclonal antibodies reactive with four distinct epitopes of the human retinoblastoma (Rb) protein", *Proceedings of the American Association for Cancer Research Annual Meeting*, 33:390 (1992).
Shew J. et al., "Antibodies detecting abnormalities of the retinoblastoma susceptibility gene pb110RB in osteosarcomas and sarcomas", *Chemical Abstracts*, vol. 111, No. 15 (Oct. 9, 1989).
Wen–Hwa L. et al., "The retinoblastoma susceptibility gene encodes a nuclear phosphoprotein associated with DNA binding activity", *Nature*, 329:642–645 (1987).

*Primary Examiner*—Lila Feisee
*Assistant Examiner*—Yvonne Eyler
*Attorney, Agent, or Firm*—Townsend and Townsend and Crew LLP

[57] ABSTRACT

This invention provides a family of monoclonal antibodies specific for epitopes of p110$^{RB}$ protein present in the nucleus. These antibodies have superior properties that prove useful for the detection of p110$^{RB}$ or its complexes with other cellular regulatory proteins in cells and in cell lysates. This invention also provides hybridoma cell lines that produce such monoclonal antibodies and methods of using these antibodies diagnostically, prognostically and therapeutically. Further, the invention provides a method for isolating proteins associated with p110$^{RB}$ proteins.

2 Claims, 6 Drawing Sheets

CHARACTERIZATION OF A NOVEL ANTI-P110$^{RB}$ MONOCLONAL ANTIBODY

FIELD OF THE INVENTION

This invention relates to monoclonal antibodies directed against the retinoblastoma protein p110$^{RB}$. More specifically, it relates to a novel monoclonal antibody having the ability to detect p110$^{RB}$ that has been previously bound by a naturally occurring or non-naturally occurring ligand.

BACKGROUND OF THE INVENTION

The retinoblastoma gene (RB) is one of the best-studied tumor suppressor genes. Mutations which prevent the normal expression of the retinoblastoma gene have been linked to the pathogenesis of several human malignancies. These include small-cell lung carcinomas, osteosarcomas, breast carcinomas, soft tissue sarcomas, bladder carcinomas, prostate carcinomas and testicular tumors.

p110$^{RB}$, the protein product of the RB (retinoblastoma) gene, specifically binds and forms a complex with several DNA tumor vital oncoproteins, including adenovirus E1A, polyomavirus Tag and papillomavirus E7. It is believed that these oncoproteins bind to and inactivate an important function of p110$^{RB}$, thereby mimicking the loss of retinoblastoma gene function. Studies have suggested that p110$^{RB}$ has intrinsic DNA-binding activity and may also interact with cellular transcription factors E2F/DRTF. Improved methods of determining the absence of p110$^{RB}$ could aid clinicians in their evaluation of patients and their decision as to appropriate treatment. Recently, evidence has become available that the loss of p110$^{RB}$ expression, as measured by immunohistochemistry, may be predictive of patient prognosis in non-small lung cancer, and in bladder cancer. It is likely that additional studies of this sort will add to the list of cancers in which loss of p110$^{RB}$ expression will be predictive of the aggressiveness of disease. Because of this, improved methods of immunohistochemistry are required to aid clinicians in their evaluation of patients and their decisions regarding aggressiveness or modality of therapy. In this case, increased intensity of available chemotherapy is one option, another option may be therapies derived from the tumor suppressor gene, RB, or its gene product p110$^{RB}$. In the latter case, lack of Rb protein expression would indicate that the patient is a candidate for RB-related therapy.

The currently available antibodies to p110$^{RB}$ are either polyclonal, and therefore, variable, or monoclonal but inappropriate because of low affinity or because they are targeted to an epitope of p110$^{RB}$ likely to be masked by cytoplasmic proteins. If such epitopes are masked by cytoplasmic proteins, therefore giving a "false negative" reading with respect to p110$^{RB}$ expression, then an incorrect therapeutic modality may be chosen. Thus, there exists a need for monoclonal antibodies reactive with p110$^{RB}$ regardless of associated cytoplasmic proteins. The present invention satisfies this need and provides related advantages as well.

SUMMARY OF THE INVENTION

This invention provides a family of monoclonal antibodies specific for epitopes of p110$^{RB}$ protein present in the nucleus. These antibodies have superior properties that prove useful for the detection of p110$^{RB}$ or its complexes with other cellular regulatory proteins in cells and in cell lysates.

This invention also provides hybridoma cell lines that produce such monoclonal antibodies and methods of using these antibodies diagnostically, prognostically and therapeutically.

Further, the invention provides a method for isolating proteins associated with p110$^{RB}$ proteins.

BRIEF DESCRIPTION OF THE FIGURES

□3C8, ΔlE5, ● PMG-3-245

□3C8, ΔlE5, ● PMG-3-245

DETAILED DESCRIPTION OF THE INVENTION

This invention provides a family of monoclonal antibodies directed at the product of the retinoblastoma gene (p110$^{RB}$). These monoclonal antibodies have been characterized and compared with respect to their ability to target intracellular p110$^{RB}$ by immunocytostaining, ELISA, immunoprecipitation and direct immunoblotting. Preliminary epitope analyses have been conducted by reaction with synthetic polypeptides or fragments of p110$^{RB}$ expressed in E. coli. Localization of one of the monoclonal antibodies (1E5) to a region between amino acid residue (aa511–aa530), within the N-terminal Tag binding domain, suggested that it may interfere in p110$^{RB}$ binding to a large T antigen (Tag). A large Tag/Rb binding assay was developed which would be suitable for screening of p110$^{RB}$ agonists or antagonists. This assay showed that Tag/Rb complexes prevented binding of 1E5, further supporting its epitope assignment to the Tag binding domain of p110$^{RB}$. Another monoclonal antibody, 3C8, which binds p110$^{RB}$ near the C-terminal end of the protein (aa886–aa905) is shown to be useful for the detection of p110$^{RB}$ in cells, or in cell lysates. Because 3C8 binds outside of regions thought to be involved in p110$^{RB}$ interactions with other cellular proteins, it may be an especially useful affinity reagent for the isolation of cellular proteins which specifically interact with p110$^{RB}$.

As used herein, the term "p110$^{RB}$" refers to the expression product of the Rb gene as noted in Lee et al., Nature 329:642–645 (1987), which is incorporated herein by reference. The numbering of the amino acid residues conforms to that of this reference [SEQ ID NO:1 and [SEQ ID NO:2].

Figure 4:
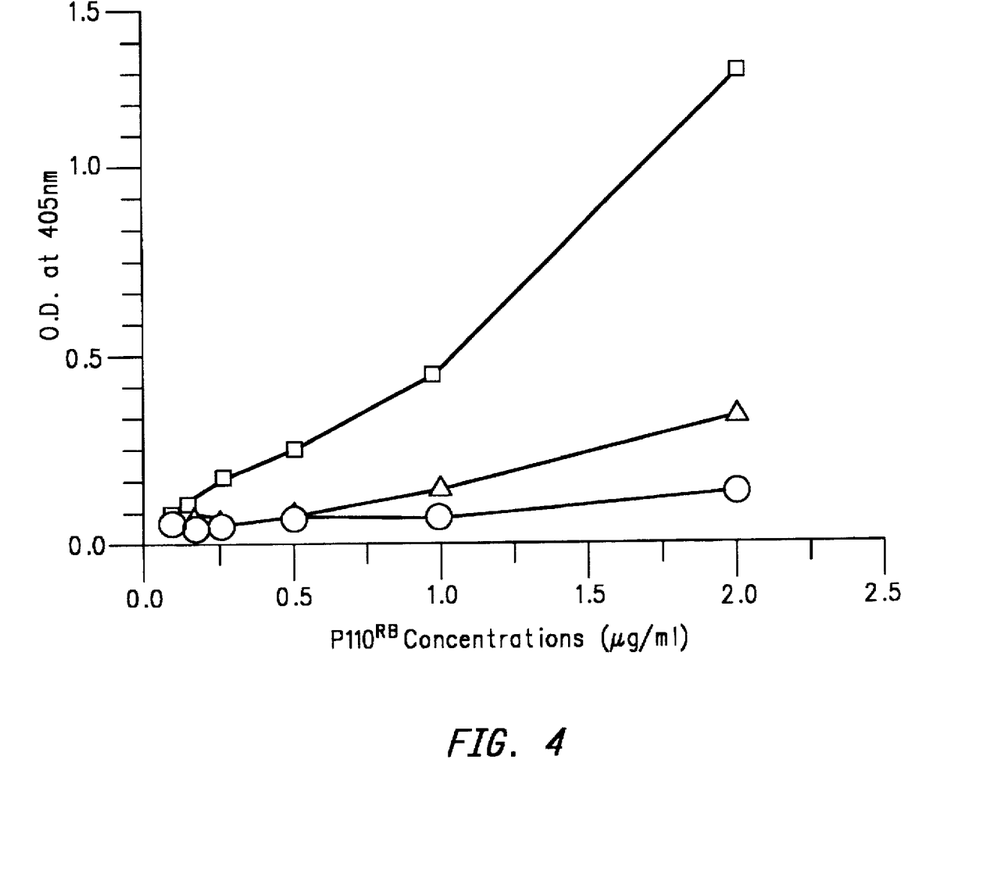
FIG. 4 shows Tag/Rb association inhibits binding of 1E5 and PMG-3-245. 0.2 ug/ml of 3C8, 1 µg/ml of PMG-3-245 and 1 µg/ml of 1E5 were used to detect bound p110$^{RB}$.

Described herein is the initial characterization of a family of monoclonal antibodies directed against $p110^{RB}$. Among these antibodies, 3C8 (ATCC Designation Number HB-12313. Deposited with the American Type Culture Collection, 12301 Parklawn Drive, Rockville, Md. 20852 on Mar. 14, 1997), which recognizes a C-terminal epitope, was compared with PMG-3-245, which recognizes an epitope near or within the first Tag binding domain of $p110^{RB}$. The results showed 3C8 can detect $p110^{RB}$ with higher sensitivity than PMG-3-245 in immunoblots, immunoprecipitation, ELISA and immunocytostaining. Previous studies indicated that the region of $p110^{RB}$ needed for binding to several DNA tumor virus oncoproteins E1A, E7 and large T antigen had been mapped in the region from amino acid residues 394 to 571 and 649 to 793, as described by Huang et al., EMBO J. 9:1815–1822 (1990) and Hu et al., EMBO J. 9:1147–1155 (1990) and incorporated herein by reference. There is also evidence that cells produce one or more proteins that interact with the Tag/E1A binding domain of $p110^{RB}$ in a manner resembling that employed by Tag and E1A (18–20, Kaelin et al., Cell 64:521–532 (1991 and Lee et al., J. Virol. 38:1064–1076 (1981) and incorporated herein by reference. If so, an antibody that interacts with this region of the $p110^{RB}$ might, preferentially or exclusively, recognize the unbound form of the $p110^{RB}$, or, alternatively, might be expected to "miss" the bound form of $p110^{RB}$, thus resulting in a false negative conclusion regarding $p110^{RB}$ expression. This assumption was confirmed by using 1E5 in a Tag/ $p110^{RB}$ binding assay (FIG. 4). 1E5, which recognizes an epitope located within the Tag binding site which is located at, within, or near aa393–aa572, failed to recognize $p110^{RB}$ in the $p110^{RB}$-Tag complex. FIG. 4 also reveals that PMG-3-245 failed to detect the bound form of $p110^{RB}$. This may be because the Tag-Rb complex sterically blocks the epitope from antibody-combining sites in this assay format with PMB-3-245, which also binds near this domain, and 1E5.

Many factors influence the reactivity of monoclonal antibodies. These include differences in affinity, contiguous vs. conformational epitopes as well as the other factors described above (e.g., association of the target protein with other cellular proteins). The monoclonal antibody, 3C8, which has strong reactivity with the C-terminus of $p110^{RB}$, should aid in the characterization of the level of $p110^{RB}$ in tumor cells. As an affinity reagent it may also allow characterization of $p110^{RB}$ associated proteins via the appropriate affinity chromatography or immunoprecipitation studies (8, as described by Hu et al., Mol. Cell. Biol. 11:5792–5799 (1991), and incorporated herein by reference. It is critical that an antibody such as 3C8 be used in such studies because it recognizes an epitope not thought to be critical for interaction of those domains of $p110^{RB}$ which interact with other cellular proteins.

Figure 1:
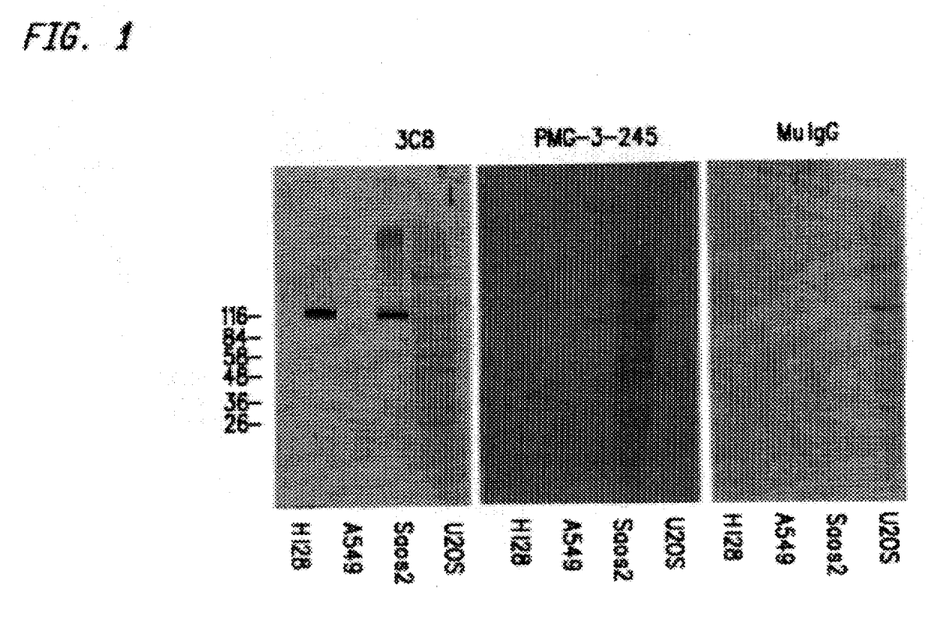
FIG. 1 shows an immunoblot analysis of p110$^{RB}$ expression in various transformed cell lines with 1 µg/ml of 3C8(A), PMG3-245(B) and MuIgG (as negative control, C). The proteins were visualized by NBT/BCIP substrate.

In order to more fully determine whether 3C8 may have advantages for evaluation of $p110^{RB}$ expression, four cell lines were examined for expression of the RB-encoded tumor suppressor protein. As expected, multiple forms of $p110^{RB}$ proteins were found in A549 and U2OS, but not in SaOS2 and H128 by direct immunoblotting with 3C8 (FIG. 1). This observation is consistent with previous studies on RB-gene expression by immunoprecipitation in these four cell lines (17, as described by Yokota et al., Oncogene 3:471–475 (1988); Shew et al., supra, 1990; Hensel et al., supra 1990, and incorporated herein by reference. However, only trace amounts of RB-encoded proteins were detected with PMG-3-245 by direct immunoblotting in these assays (FIG. 1). These data show that both 3C8 and PMG-3-245 were able to recognize the native forms of $p110^{RB}$ in cell lysates, and that monoclonal antibody 3C8 demonstrated greater sensitivity for recognition of $p110^{RB}$ than did PMG-3-245. The same pattern is also reported here for immunocytochemical staining. This may be due to the stronger affinity of 3C8 for $p110^{RB}$ and/or the different epitopes recognized by these monoclonal antibodies. Previous studies have shown that functional loss of the RB gene may contribute significantly to tumor progression (11,12, as described by Cance et al., N. Engl. J. Med. 3232:1457–1462 (1990) and incorporated herein by reference. To resolve whether RB plays a key role in carcinogenesis, an accurate and fast screening method should be established to reflect the true frequency of inactivation of RB in cancers. Molecular genetic approaches, such as Southern analysis, may not detect small molecular alterations (6,12, Figge et al., Amer. J. Pathology 139:1213–1219 (1991) and Horowitz et al., Science 243:937–943 (1989) and incorporated herein by reference. Also, contamination of tumor tissue with normal cells may lead to underestimation of the degree of abnormalities and confound Southern, Northern, or PCR-based analysis (6,12, as described by Murakami et al., Cancer Res. 51:5520–5525 (1991).

Immunohistochemical staining represents the most reliable method for analyzing tumor samples for $p110^{RB}$ expression because this method allows direct visualization of tumor cells within biopsy specimens. The availability of 3C8 provides a potentially better means to screen for $p110^{RB}$ expression in cell lines and histological specimens. The use of monoclonal antibody 3C8 may lead to a more accurate estimate of $p110^{RB}$ expression in tumor samples and therefore may allow for a more critical analysis of the prognostic value of $p110^{RB}$ analysis in human cancers.

The following Examples are intended to illustrate, but not limit the invention.

EXAMPLE I

Protein Purification: The recombinant baculovirus vector, pAcYM1/RB2.8, encoding $p110^{RB}$, was expressed in AcNPV-Y4 insect cells, according to the method of Wang et al., Cell Growth and Differentiation 1:429–437 (1990), which is incorporated herein by reference. Cells were treated with lysis buffer (25 mM Tris-HCl, pH8.0/150 mM NaCl/ 0.5% NP40/50 mM NaF/10 ug/ml/aprotinin/10 ug/ml leupeptin) on ice for 1 hour. The $p110^{RB}$ was purified by sequential chromatography on CM Sepharose CL6B and DEAE Sepharose CL6B. Column fractions were analyzed by SDS-polyacrylamide gel electrophoresis (SDS-PAGE) and immunoblotting. The fractions that contained pure $p110^{RB}$ were pooled and concentrated. For preparation of TrpE-RB fusion proteins, RB cDNA fragments AvaII/BglII/ HindIII (exon 19–27) expression plasmids were transfected into E. coli as described in Wang et al., Cell Growth and Differentiation 1:233–239 (1990), and incorporated herein by reference. The transfected cells were treated with lysis buffer and the fusion proteins (pRB01-10, pRB10-19, pRB23-27 and pRB 19-27) were purified by continuous-elution electrophoresis (Model 491 Prep Cell, BioRad, Richmond, Calif.).

Hybridoma Production: Hybridomas were generated as described in Godwing, Monoclonal antibodies: Principles and practice, Academic Press Inc. 1983, which is incorporated herein by reference. Briefly, purified $p110^{RB}$, pRB 01-10 (aa44–aa330) and pRB 19-27 (aa612–aa928) were used to immunize Balb/c mice by intraperitoneal injection.

After high titers of antibodies specific for p110$^{RB}$, pRB 01–10 and pRB 19–27 were detected, a representative mouse was sacrificed and hybridomas were prepared by fusing mouse spleen cells to Sp2/O cells. Positive clones were identified by the enzyme linked immunoadsorbent assay and immunoblotting. All hybridomas were subcloned and propagated in Dulbecco's modified Eagle's medium supplemented with 10% fetal calf serum. Single cell cloning was done by limiting dilution. Antibody isotypes were determined using a kit provided by Zymed Laboratories Inc., San Francisco, Calif.

Immunoblotting: Purified p110$^{RB}$ fragments were prepared as fusion proteins from *E. coli* lysates. These included aa41–aa928, aa41–aa330, aa612–aa928 and aa776–aa928. Each fusion protein was employed for initial epitope screening and monoclonal antibody characterization. Cells were solubilized in 50 mM Tris-HCl pH 7.5/250 mM NaCl/0.1% NP40/50 mM NaF/5 mM EDTA/10 ug/ml aprotinin/10 ug/ml leupeptin on ice for 2–20 minutes and protein was quantitated (BioRad, Richmond, Calif.) was employed for hybridoma screening. The protein was then electrotransferred to an Imobilon P membrane (Millipore, South San Francisco, Calif.). After primary antibody incubation, The membranes were washed three times, 10 minutes each, with 0.05% Tween-20 in PBS. Goat anti-mouse IgG conjugated to alkaline phosphatase (Promega, Madison, Wis.), diluted 1:7500 in 0.5% BSA/PBS was added to immunoblots for 1 hour at 24° C. Blots were again washed in 0.5% BSA/PBS three times for 10 minutes each. Alkaline phosphatase substrate, NBT/BCIP (nitro blue tetrazolium/5-bromo-4-chloro-3-indolyl-phosphate; Promega) was then added and incubated for 15–30 minutes.

Immunoprecipitation: A previously described protocol was employed as described in Lee et al., J. Virol. 38:1064–1076 (1981), and incorporated herein by reference. Purified monoclonal antibody (10 μg) was added into 1 mg of U2OS total cell lysate. After a 30 minute incubation on ice, protein A-sepharose 4B beads or protein G-sepharose 4B beads (Pharmacia, Milwaukee, Wis.) were added to precipitate the immune complex. The immunoprecipitates then were analyzed by 8–16% SDS-PAGE and immunoblotting.

Immunocytochemical staining: Immunocytochemical analysis was performed using monoclonal antibodies directed against p110$^{RB}$ and nonspecific control antibody (MuIgG) on formalin-fixed cells. The avidin-biotin complex-immunoperoxidase technique as described in Cordon-Cardo et al., Amer. J. Pathol. 126:269–284 (1987), and incorporated herein by reference; (Vector Laboratories, Burlingame, Calif.) was used to visualize antibody binding. Diaminobenzidine was employed as the final chromogen.

Enzyme linked immunoadsorbent assay (ELISA): Purified p110$^{RB}$, or purified fusion proteins, were used to develop an ELISA for hybridoma screening and monoclonal antibody characterization. 50 μl of coating buffer (25 mmol/l carbonate buffer, pH 9.6) containing 50 ng of purified p110$^{RB}$ or fusion proteins were coated on microtiter plates (Costar, Pleasanton, Calif.) overnight at 4° C. An optimized ELISA protocol was followed as described in Campbell et al., Monoclonal Antibody Technology; Laboratory Techniques in Biochemistry and Molecular Biology (1987) and incorporated herein by reference.

Tag/Rb binding assay: A modified ELISA protocol was employed. 50 μl of 1 μg/ml purified Tag in coating buffer was bound to wells in microtiter plates at 4° C. overnight. After blocking with BSA (10 mg/ml in PBS) various concentrations (2 μg/ml to 0.016 μg/ml) of purified p110$^{RB}$ were added into each well. The plate was incubated for 1 hour at room temperature. After washing four times with PBS/ Tween-20, biotinylated 3C8, 1E5 or PMG-3-245 was added to the appropriate wells and the plate was incubated for an additional 1 hour at room temperature. The plate was then washed four times as described above. 1:2500 dilution of Streptavidin-POD (Boehringer Mannheim GmbH, Chicago, Ill.) was added to the wells and was incubated for 1 hour at room temperature. ABTS(2.2-Azino-bis(3-ethylbenzthiazoline-6-sulfonic acid)) was used as chromogen. Color development was measured after 20–30 minutes incubation and the absorbance (405 nm) was determined by microtiter plate autoreader (Coulter microplate reader, Molecular Devices, Menlo Park, Calif.).

Affinity measurements: The Kd values for 3C8 and PMG-3-245 were determined by ELISA as described by Friguet et al., J. Immuno. Methods 77 (1985), and incorporated herein by reference. First, a constant concentration of 3C8 or PMG-3-245 was incubated overnight in solution with various concentrations of p110$^{RB}$. After equilibrium was reached, the unbound antibody was determined by ELISA protocol as described above.

EXAMPLE II

Figure 2:
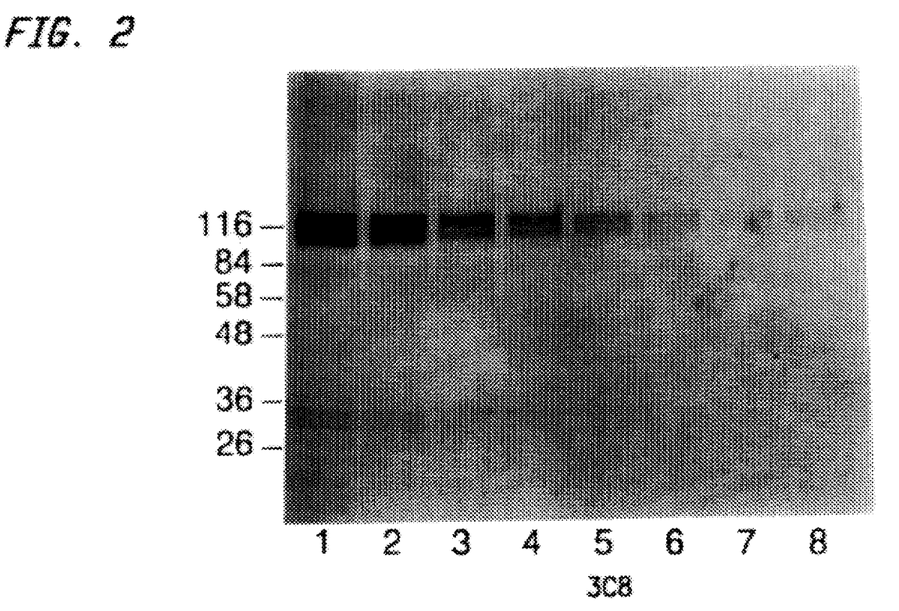
FIG. 2 shows 20 µl of A549 cell lysate (started from 1 mg/ml, lane 1) with 2-fold serial dilutions were immunoblotted and detected with antibody 3C8 (2 µg/ml).
Figure 3:
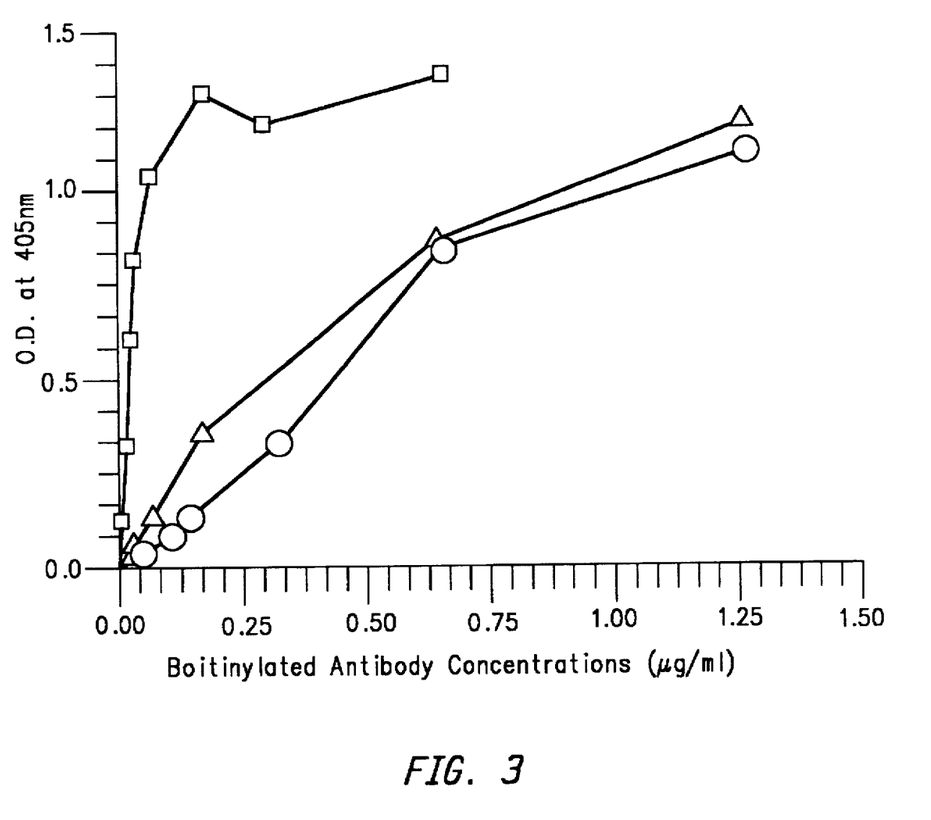
FIG. 3 shows ELISA for biotinylated 3C8, 1E5 and PMG-3-245. Various concentrations of biotinylated anti-Rb antibodies were titrated in p110$^{RB}$ coated plates. ELISA protocol was followed as described in the Materials and Methods section infra.

Generation and Initial Characterization of Monoclonal Antibodies Directed Against p110$^{RB}$ Purified p110$^{RB}$ was used to immunize Balb/c mice. After the third boost, the most responsive mouse, as determined by ELISA, was chosen for the preparation of hybridomas. All of the monoclonal antibodies generated by purified p110$^{RB}$ were found to recognize only sequences within p110$^{RB}$ amino acid residues 330 to 612, determined by standard immunoblot techniques. In order to obtain antibodies that would recognize different regions of p110$^{RB}$, *E. coli* TrpE-RB fusion proteins encompassing amino acid residues 41 to 330 and 612 to 928 respectively, were used as immunogens. This provided a means for focusing antibody production to regions of p110$^{RB}$ which is important for prognostic applications. The initial screening procedures required positive ELISA and immunoblotting results. After single cell cloning of positive hybridomas the locations of the respective epitopes on p110$^{RB}$ were determined by competition ELISA and immunoprecipitation with fusion proteins and/or with synthetic polypeptides as described in Table 1. Six independent clones were selected as representative clones recognizing different regions of p110$^{RB}$. To further characterize these six antibodies, each was tested for its ability to recognize p110$^{RB}$ by immunoblotting, ELISA, immunoprecipitation and immunocytochemical staining assays. All of the tested antibodies were able to recognize native p110$^{RB}$ as judged by their activity in immunoprecipitation assays (summarized in Table 1 ). One of the antibodies, 3C8, recognized an epitope contained within amino acid residues 886 to 905 of p110$^{RB}$, and demonstrated very strong immunoreactivity with p110$^{RB}$ (summarized in Table 1). To further characterize 3C8, U-2OS and A549 which express a normal p110$^{RB}$ (17,29); and SaOS2 and H128 which have previously been reported to express low levels of an altered RB gene product as described in Shew et al., Proc. Natl. Aced. Sci. USA 87:6–10 (1990); Hensel et al., Cancer Res. 50:3067–3072 (1990) and incorporated herein by reference, were immunoblotted directly with 3C8 (FIG. 1). The results showed a tight cluster of bands consistent with the presence of phosphorylated and unphosphorylated p110$^{RB}$ proteins with apparent molecular weights between 110 and 116 kDa in both U-2OS and A549 cell lysates. In contrast, none of these bands was detected in SaOS2 and H128 bells. Under these conditions, PMG-3-245 failed to detect significant p110$^{RB}$ in U-2OS or A549 cells (FIG. 1). This indicated that the 3C8 antibody may be more sensitive than PMG-3-245 for immunoblotting analyses. To test this possibility further, A549 cell lysate (1 mg/ml 2-fold serial dilutions) was immunoblotted with antibodies 3C8 or PMG-3-245 (FIG. 2). $p110^{RB}$ proteins were readily detected by 3C 8 even when total lysate protein loaded per lane was as low as 0.625 µg, while PMG-3-245 only slightly revealed a signal of $p110^{RB}$ even in the undiluted total lysate (20 µg loaded). ELISA (FIG. 3) data also suggested that 3C8 may show a higher affinity for $p110^{RB}$ than PMG-3-245. These results were confirmed by direct measurements of the dissociation constant of antigen-antibody equilibria. The Kd values were calculated as described by Friguet et al., supra 1985, and incorporated herein by reference. A Kd value of $2.9 \times 10^{-9}$M for 3C8 and $6.2 \times 10^{-9}$M for PMG-3-245 were determined which supported other data that 3C8 appears to have improved binding for $p110^{RB}$ than PMG-3-245. However, it is not claims that affinity alone is important, as the physical properties of the monoclonal antibody as well as its epitope, are probably important contributing factors.

TABLE I

Characterization of Anti RB Monoclonal Antibodies

| MOAB | Binding Site Amino Acid (EXON) | ELISA | IB | IP/IB | IS | Isotypes |
|---|---|---|---|---|---|---|
| 3C8 | 886–905 (25–27) | +++ | +++ | +++ | +++ | $IgG_{2a}$ |
| 4G2 | 41–330 (1–10) | ++ | ++ | + | ++ | $IgG_1$ |
| 7F12 | 41–330 (1–10) | + | ++ | + | ++ | $IgG_1$ |
| 1D1 | 571–590 (18) | + | + | + | − | $IgG_1$ |
| 1E5* | 511–530 (17) | +++ | +++ | +++ | − | $IgG_1$ |
| 1G5 | 371–390 (11–12) | ++ | ++ | ++ | ++ | $IgG_1$ |

Elisa: $p110^{RB}$ coated on plates
IB: Immunoblotting (Baculovirus lysate or purified $p110^{RB}$)
IP/IB: Immunoprecipitation-Immunoblotting (Baculovirus lysate or purified $p110^{RB}$) detection by 3C8
IS: Immunocytochemical staining (U2OS cell line)
ND: Not done.
*: This monoclonal antibody recognized Tag binding region of $p110^{RB}$, which is located at, within or near aa393-aa572.

The Tag/Rb binding assay (FIG. 4) demonstrates that 3C8 can recognize $p110^{RB}$ in a Tag-$p110^{RB}$ complex. However, the binding of PMG-3-245 and 1E5 to $p110^{RB}$ were abrogated by the Tag-$p110^{RB}$ association. The results support the proposal that 3C8 may be superior for detection of $p110^{RB}$ in cell lysates to 1E5 or PMG-3-245 because it reacts outside the regions of $p110^{RB}$ which interact with other regulatory proteins. The relative affinity for $p110^{RB}$ of 3C8 may also be an important determining factor.

Figure 5:
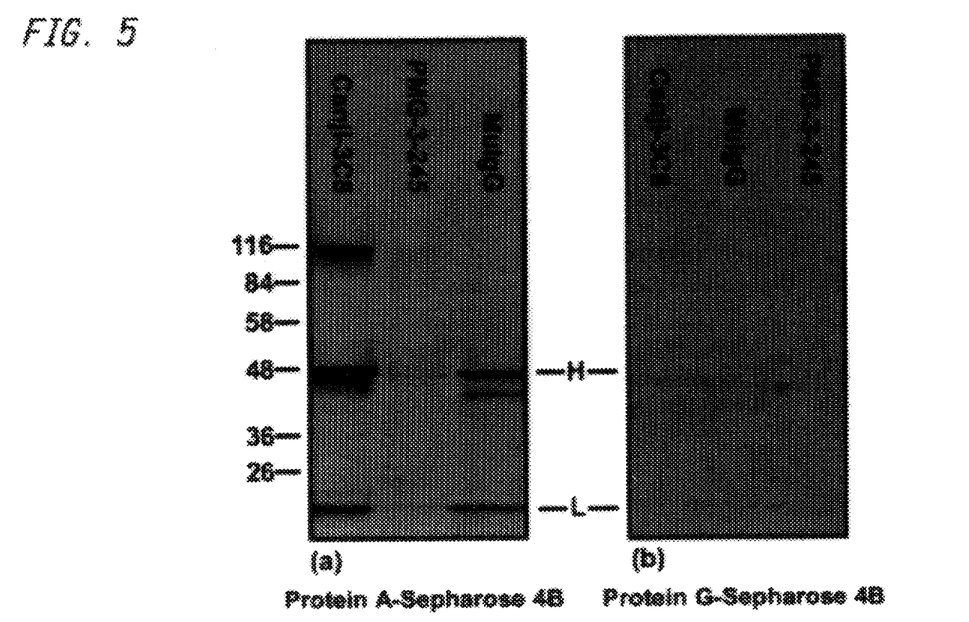
FIG. 5 shows identification of p110$^{RB}$ in U2OS cell lysate with 3C8, PMG-3-245 and MuIgG2a (as a negative control). Protein A-Sepharose beads (a) or protein G-sapharoes beads (b) were employed to immunoprecipitate immunocomplexes. The immunoprecipitated proteins were analyzed by 8–16% gradient SDS-PAGE and immunoblotted. H:heavy chain of MuIgG. L:light chain of MuIgG.

The characterization of 3C8 was also investigated by immunoprecipitation and immunocytochemical staining. As shown in FIG. 5a, nonradiolabeled immunoprecipitation/immunoblotting assays indicate that the efficiency of 3C8 in immunoprecipitation studies of native $p110^{RB}$ from U2OS tumor cells apparently was higher than with PMG-3-245 (FIG. 5). Protein G-sepharose 4B was used to exclude the possibility of the different affinity of protein A-sepharose RB to different subclasses of the antibodies. (3C8 is $IgG_{2a}$, and PMG-3-245 is $IgG_1$). A band of $p110^{RB}$ was easily observed when protein-A-sepharose 4B was used (FIG. 5a,b). These results suggest that 3C8 can immunoprecipitate $p110^{RB}$ more effectively than PMG-3-245 and that the efficiency of immunoprecipitation is unrelated to the isotype of 3C8.

Figure 6:
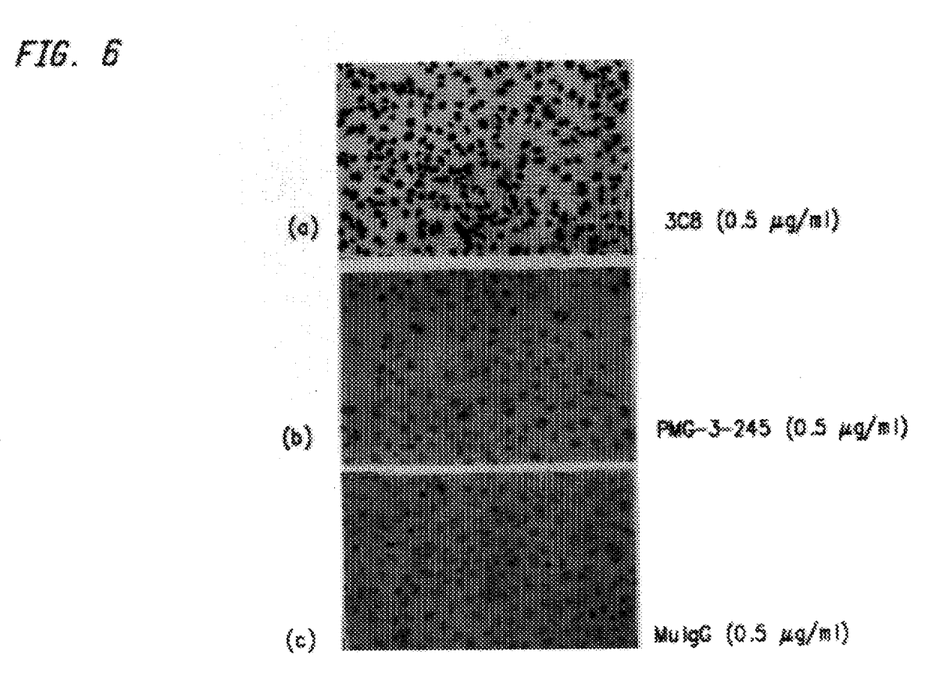
FIG. 6 shows immunocytostaining with 3C8, PMG-3-245 and nonspecific control antibody (MuIgG) on a 9 mm×9 mm chamber slide, containing 2×10$^5$ formalin-fixed U2OS osteosarcoma cancer cells. 0.5 µg/ml concentration of each antibody was employed as primary antibody. Diaminobenzidine was used as the final chromogen.

Because tumor cell $p110^{RB}$ immunostaining is useful as a prognostic/diagnostic method(12), the monoclonal antibodies 3C8 and PMG-3-245 were compared for their immunocytochemical staining abilities (FIG. 6). U-2OS tumor cells were immunostained with 3C8 and PMG-3-245 monoclonal antibodies. While there is no obvious difference in immunocytochemical staining while using high concentrations (4 µg/ml) of PMG-3-245 or 3C8, staining with 3C8 gave more intense staining when both monoclonal antibodies were compared at 0.5 µg/ml (FIG. 6).

Although the invention has been described with reference to the presently-preferred embodiments, it should be understood that various modifications can be made without departing from the spirit of the invention. Accordingly, the invention is limited only by the following claims.

We claim:

1. An antibody which specifically binds an epitope comprising amino acid residues 886 to 905 of the human wild-type retinoblastoma (RB) tumor suppressor protein (SEQ. ID No. 1), wherein the antibody is the monoclonal antibody designated as 3C8.

2. A hybridoma producing the monoclonal antibody of claim 1, wherein the hybridoma is ATCC HB-12312.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 928 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:1:

| | | | | | | | | | | | | | | |
|---|---|---|---|---|---|---|---|---|---|---|---|---|---|---|
| Met 1 | Pro | Pro | Lys | Thr 5 | Pro | Arg | Lys | Thr 10 | Ala | Thr | Ala | Ala 15 | Ala | Ala |
| Ala | Ala | Glu | Pro 20 | Pro | Ala | Pro | Pro 25 | Pro | Pro | Pro | Pro 30 | Glu | Glu | Asp |
| Pro | Glu | Gln 35 | Asp | Ser | Gly | Pro 40 | Glu | Asp | Leu | Pro 45 | Leu | Val | Arg | Leu | Glu |
| Phe | Glu 50 | Glu | Thr | Glu | Glu | Pro 55 | Asp | Phe | Thr | Ala 60 | Leu | Cys | Gln | Lys | Leu |
| Lys 65 | Ile | Pro | Asp | His | Val 70 | Arg | Glu | Arg | Ala | Trp 75 | Leu | Thr | Trp | Glu | Lys 80 |
| Val | Ser | Ser | Val | Asp 85 | Gly | Val | Leu | Gly | Gly 90 | Tyr | Ile | Gln | Lys | Lys 95 |
| Glu | Leu | Trp | Gly 100 | Ile | Cys | Ile | Phe | Ile 105 | Ala | Ala | Val | Asp | Leu 110 | Asp | Glu |
| Met | Ser | Phe 115 | Thr | Phe | Thr | Glu | Leu 120 | Gln | Lys | Asn | Ile 125 | Glu | Ile | Ser | Val |
| His | Lys 130 | Phe | Phe | Asn | Leu | Leu 135 | Lys | Glu | Ile | Asp | Thr 140 | Ser | Thr | Lys | Val |
| Asp 145 | Asn | Ala | Met | Ser | Arg 150 | Leu | Leu | Lys | Lys | Tyr 155 | Asp | Val | Leu | Phe 160 | Ala |
| Leu | Phe | Ser | Lys | Leu 165 | Glu | Arg | Thr | Cys | Glu 170 | Leu | Ile | Tyr | Leu 175 | Thr | Gln |
| Pro | Ser | Ser | Ser 180 | Ile | Ser | Thr | Glu | Ile 185 | Asn | Ser | Ala | Leu | Val 190 | Leu | Lys |
| Val | Ser | Trp 195 | Ile | Thr | Phe | Leu | Leu 200 | Ala | Lys | Gly | Glu | Val 205 | Leu | Gln | Met |
| Glu | Asp 210 | Asp | Leu | Val | Ile | Ser 215 | Phe | Gln | Leu | Met | Leu 220 | Cys | Val | Leu | Asp |
| Tyr 225 | Phe | Ile | Lys | Leu | Ser 230 | Pro | Pro | Met | Leu | Leu 235 | Lys | Glu | Pro | Tyr | Lys 240 |
| Thr | Ala | Val | Ile | Pro 245 | Ile | Asn | Gly | Ser | Pro 250 | Arg | Thr | Pro | Arg | Arg 255 | Gly |
| Gln | Asn | Arg | Ser 260 | Ala | Arg | Ile | Ala | Lys 265 | Gln | Leu | Glu | Asn | Asp 270 | Thr | Arg |
| Ile | Ile | Glu 275 | Val | Leu | Cys | Lys | Glu 280 | His | Glu | Cys | Asn | Ile 285 | Asp | Glu | Val |
| Lys | Asn 290 | Val | Tyr | Phe | Lys | Asn 295 | Phe | Ile | Pro | Phe | Met 300 | Asn | Ser | Leu | Gly |
| Leu 305 | Val | Thr | Ser | Asn | Gly 310 | Leu | Pro | Glu | Val | Glu 315 | Asn | Leu | Ser | Lys 320 | Arg |
| Tyr | Glu | Glu | Ile | Tyr 325 | Leu | Lys | Asn | Lys | Asp 330 | Leu | Asp | Ala | Arg | Leu 335 | Phe |
| Leu | Asp | His | Asp 340 | Lys | Thr | Leu | Gln | Thr 345 | Asp | Ser | Ile | Asp | Ser 350 | Phe | Glu |
| Thr | Gln | Arg 355 | Thr | Pro | Arg | Lys | Ser 360 | Asn | Leu | Asp | Glu | Glu 365 | Val | Asn | Val |
| Ile | Pro 370 | Pro | His | Thr | Pro | Val 375 | Arg | Thr | Val | Met | Asn 380 | Thr | Ile | Gln | Gln |
| Leu 385 | Met | Met | Ile | Leu | Asn 390 | Ser | Ala | Ser | Asp | Gln 395 | Pro | Ser | Glu | Asn | Leu 400 |
| Ile | Ser | Tyr | Phe | Asn 405 | Asn | Cys | Thr | Val | Asn 410 | Pro | Lys | Glu | Ser | Ile 415 | Leu |
| Lys | Arg | Val | Lys | Asp | Ile | Gly | Tyr | Ile | Phe | Lys | Glu | Lys | Phe | Ala | Lys |

-continued

|   |   |   | 420 |   |   |   | 425 |   |   |   | 430 |   |   |
|---|---|---|---|---|---|---|---|---|---|---|---|---|---|
| Ala | Val | Gly | Gln | Gly | Cys | Val | Glu | Ile | Gly | Ser | Gln | Arg | Tyr | Lys | Leu |
|   |   | 435 |   |   |   | 440 |   |   |   | 445 |   |   |   |
| Gly | Val | Arg | Leu | Tyr | Tyr | Arg | Val | Met | Glu | Ser | Met | Leu | Lys | Ser | Glu |
|   |   | 450 |   |   | 455 |   |   |   | 460 |   |   |   |   |
| Glu | Glu | Arg | Leu | Ser | Ile | Gln | Asn | Phe | Ser | Lys | Leu | Leu | Asn | Asp | Asn |
| 465 |   |   |   | 470 |   |   |   | 475 |   |   |   | 480 |
| Ile | Phe | His | Met | Ser | Leu | Leu | Ala | Cys | Ala | Leu | Glu | Val | Val | Met | Ala |
|   |   |   | 485 |   |   |   | 490 |   |   |   | 495 |
| Thr | Tyr | Ser | Arg | Ser | Thr | Ser | Gln | Asn | Leu | Asp | Ser | Gly | Thr | Asp | Leu |
|   |   | 500 |   |   |   | 505 |   |   |   | 510 |   |
| Ser | Phe | Pro | Trp | Ile | Leu | Asn | Val | Leu | Asn | Leu | Lys | Ala | Phe | Asp | Phe |
|   |   | 515 |   |   |   | 520 |   |   |   | 525 |   |   |
| Tyr | Lys | Val | Ile | Glu | Ser | Phe | Ile | Lys | Ala | Glu | Gly | Asn | Leu | Thr | Arg |
|   | 530 |   |   |   | 535 |   |   |   | 540 |   |   |
| Glu | Met | Ile | Lys | His | Leu | Glu | Arg | Cys | Glu | His | Arg | Ile | Met | Glu | Ser |
| 545 |   |   |   | 550 |   |   | 555 |   |   |   | 560 |
| Leu | Ala | Trp | Leu | Ser | Asp | Ser | Pro | Leu | Phe | Asp | Leu | Ile | Lys | Gln | Ser |
|   |   |   | 565 |   |   |   | 570 |   |   |   | 575 |
| Lys | Asp | Arg | Glu | Gly | Pro | Thr | Asp | His | Leu | Glu | Ser | Ala | Cys | Pro | Leu |
|   |   | 580 |   |   |   | 585 |   |   |   | 590 |   |
| Asn | Leu | Pro | Leu | Gln | Asn | Asn | His | Thr | Ala | Ala | Asp | Met | Tyr | Leu | Ser |
|   |   | 595 |   |   |   | 600 |   |   |   | 605 |   |
| Pro | Val | Arg | Ser | Pro | Lys | Lys | Lys | Gly | Ser | Thr | Thr | Arg | Val | Asn | Ser |
|   | 610 |   |   |   | 615 |   |   |   | 620 |   |   |
| Thr | Ala | Asn | Ala | Glu | Thr | Gln | Ala | Thr | Ser | Ala | Phe | Gln | Thr | Gln | Lys |
| 625 |   |   |   | 630 |   |   |   | 635 |   |   |   | 640 |
| Pro | Leu | Lys | Ser | Thr | Ser | Leu | Ser | Leu | Phe | Tyr | Lys | Lys | Val | Tyr | Arg |
|   |   |   | 645 |   |   |   | 650 |   |   |   | 655 |
| Leu | Ala | Tyr | Leu | Arg | Leu | Asn | Thr | Leu | Cys | Glu | Arg | Leu | Leu | Ser | Glu |
|   |   | 660 |   |   |   | 665 |   |   |   | 670 |   |
| His | Pro | Glu | Leu | Glu | His | Ile | Ile | Trp | Thr | Leu | Phe | Gln | His | Thr | Leu |
|   |   | 675 |   |   |   | 680 |   |   |   | 685 |
| Gln | Asn | Glu | Tyr | Glu | Leu | Met | Arg | Asp | Arg | His | Leu | Asp | Gln | Ile | Met |
|   | 690 |   |   |   | 695 |   |   |   | 700 |
| Met | Cys | Ser | Met | Tyr | Gly | Ile | Cys | Lys | Val | Lys | Asn | Ile | Asp | Leu | Lys |
| 705 |   |   |   | 710 |   |   |   | 715 |   |   |   | 720 |
| Phe | Lys | Ile | Ile | Val | Thr | Ala | Tyr | Lys | Asp | Leu | Pro | His | Ala | Val | Gln |
|   |   |   | 725 |   |   |   | 730 |   |   |   | 735 |
| Glu | Thr | Phe | Lys | Arg | Val | Leu | Ile | Lys | Glu | Glu | Glu | Tyr | Asp | Ser | Ile |
|   |   | 740 |   |   |   | 745 |   |   |   | 750 |   |
| Ile | Val | Phe | Tyr | Asn | Ser | Val | Phe | Met | Gln | Arg | Leu | Lys | Thr | Asn | Ile |
|   | 755 |   |   |   | 760 |   |   |   | 765 |   |   |
| Leu | Gln | Tyr | Ala | Ser | Thr | Arg | Pro | Pro | Thr | Leu | Ser | Pro | Ile | Pro | His |
|   | 770 |   |   |   | 775 |   |   |   | 780 |   |   |
| Ile | Pro | Arg | Ser | Pro | Tyr | Lys | Phe | Pro | Ser | Ser | Pro | Leu | Arg | Ile | Pro |
| 785 |   |   |   | 790 |   |   |   | 795 |   |   |   | 800 |
| Gly | Gly | Asn | Ile | Tyr | Ile | Ser | Pro | Leu | Lys | Ser | Pro | Tyr | Lys | Ile | Ser |
|   |   |   | 805 |   |   |   | 810 |   |   |   | 815 |
| Glu | Gly | Leu | Pro | Thr | Pro | Thr | Lys | Met | Thr | Pro | Arg | Ser | Arg | Ile | Leu |
|   |   | 820 |   |   |   | 825 |   |   |   | 830 |   |
| Val | Ser | Ile | Gly | Glu | Ser | Phe | Gly | Thr | Ser | Glu | Lys | Phe | Gln | Lys | Ile |
|   |   | 835 |   |   |   | 840 |   |   |   | 845 |   |

| | | | | | | | | | | | | |
|---|---|---|---|---|---|---|---|---|---|---|---|---|
| Asn | Gln | Met | Val | Cys | Asn | Ser | Asp | Arg | Val | Leu | Lys | Arg | Ser | Ala | Glu |
| | 850 | | | | 855 | | | | | 860 | | |
| Gly | Ser | Asn | Pro | Pro | Lys | Pro | Leu | Lys | Lys | Leu | Arg | Phe | Asp | Ile | Glu |
| 865 | | | | | 870 | | | | | 875 | | | | | 880 |
| Gly | Ser | Asp | Glu | Ala | Asp | Gly | Ser | Lys | His | Leu | Pro | Gly | Glu | Ser | Lys |
| | | | | 885 | | | | | 890 | | | | | 895 |
| Phe | Gln | Gln | Lys | Leu | Ala | Glu | Met | Thr | Ser | Thr | Arg | Thr | Arg | Met | Gln |
| | | | 900 | | | | | 905 | | | | 910 | |
| Lys | Gln | Lys | Met | Asn | Asp | Ser | Met | Asp | Thr | Ser | Asn | Lys | Glu | Glu | Lys |
| | | 915 | | | | | 920 | | | | | 925 |

( 2 ) INFORMATION FOR SEQ ID NO:2:

( i ) SEQUENCE CHARACTERISTICS:
        ( A ) LENGTH: 2994 base pairs
        ( B ) TYPE: nucleic acid
        ( C ) STRANDEDNESS: double
        ( D ) TOPOLOGY: linear     ( i i ) MOLECULE TYPE: DNA (cDNA)

( x i ) SEQUENCE DESCRIPTION: SEQ ID NO:2:

```
TTCCGGTTTT TCTCAGGGGA CGTTGAAATT ATTTTTGTAA CGGGAGTCGG GAGAGGACGG       60
GGCGTGCCCC GCGTGCGCGC GCGTCGTCCT CCCCGGCGCT CCTCCACAGC TCGCTGGCTC      120
CCGCCGCGGA AAGGCGTCAT GCCGCCCAAA ACCCCCCGAA AAACGGCCGC CACCGCCGCC      180
GCTGCCGCCG CGGAACCCCC GGCACCGCCG CCGCCGCCCC CTCCTGAGGA GGACCCAGAG      240
CAGGACAGCG GCCCGGAGGA CCTGCCTCTC GTCAGGCTTG AGTTTGAAGA AACAGAAGAA      300
CCTGATTTTA CTGCATTATG TCAGAAATTA AAGATACCAG ATCATGTCAG AGAGAGAGCT      360
TGGTTAACTT GGGAGAAAGT TTCATCTGTG GATGGAGTAT GGGAGGTTA TATTCAAAAG       420
AAAAAGGAAC TGTGGGGAAT CTGTATCTTT ATTGCAGCAG TTGACCTAGA TGAGATGTCG      480
TTCACTTTTA CTGAGCTACA GAAAACATA GAAATCAGTG TCCATAAATT CTTTAACTTA       540
CTAAAAGAAA TTGATACCAG TACCAAAGTT GATAATGCTA TGTCAAGACT GTTGAAGAAG      600
TATGATGTAT TGTTTGCACT CTTCAGCAAA TTGGAAAGGA CATGTGAACT TATATATTTG      660
ACACAACCCA GCAGTTCGAT ATCTACTGAA ATAAATTCTG CATTGGTGCT AAAAGTTTCT      720
TGGATCACAT TTTATTAGC TAAAGGGGAA GTATTACAAA TGGAAGATGA TCTGGTGATT       780
TCATTTCAGT TAATGCTATG TGTCCTTGAC TATTTTATTA AACTCTCACC TCCCATGTTG      840
CTCAAAGAAC CATATAAAAC AGCTGTTATA CCCATTAATG GTTCACCTCG AACACCCAGG      900
CGAGGTCAGA ACAGGAGTGC ACGGATAGCA AAACAACTAG AAAATGATAC AAGAATTATT      960
GAAGTTCTCT GTAAAGAACA TGAATGTAAT ATAGATGAGG TGAAAAATGT TTATTTCAAA     1020
AATTTTATAC CTTTTATGAA TTCTCTTGGA CTTGTAACAT CTAATGGACT TCCAGAGGTT     1080
GAAAATCTTT CTAAACGATA CGAAGAAATT TATCTTAAAA ATAAAGATCT AGATGCAAGA     1140
TTATTTTTGG ATCATGATAA AACTCTTCAG ACTGATTCTA TAGACAGTTT TGAAACACAG     1200
AGAACACCAC GAAAAAGTAA CCTTGATGAA GAGGTGAATG TAATTCCTCC ACACACTCCA     1260
GTTAGGACTG TTATGAACAC TATCCAACAA TTAATGATGA TTTTAAATTC AGCAAGTGAT     1320
CAACCTTCAG AAAATCTGAT TTCCTATTTT AACAACTGCA CAGTGAATCC AAAAGAAAGT     1380
ATACTGAAAA GAGTGAAGGA TATAGGATAC ATCTTTAAAG AGAAATTTGC TAAAGCTGTG     1440
GGACAGGGTT GTGTCGAAAT TGGATCACAG CGATACAAAC TTGGAGTTCG CTTGTATTAC     1500
CGAGTAATGG AATCCATGCT TAAATCAGAA GAAGAACGAT TATCCATTCA AAATTTTAGC     1560
```

-continued

| | | | | | |
|---|---|---|---|---|---|
| AAACTTCTGA | ATGACAACAT | TTTTCATATG | TCTTTATTGG | CGTGCGCTCT | TGAGGTTGTA | 1620
| ATGGCCACAT | ATAGCAGAAG | TACATCTCAG | AATCTTGATT | CTGGAACAGA | TTTGTCTTTC | 1680
| CCATGGATTC | TGAATGTGCT | TAATTTAAAA | GCCTTTGATT | TTTACAAAGT | GATCGAAAGT | 1740
| TTTATCAAAG | CAGAAGGCAA | CTTGACAAGA | GAAATGATAA | AACATTTAGA | ACGATGTGAA | 1800
| CATCGAATCA | TGGAATCCCT | TGCATGGCTC | TCAGATTCAC | CTTTATTTGA | TCTTATTAAA | 1860
| CAATCAAAGG | ACCGAGAAGG | ACCAACTGAT | CACCTTGAAT | CTGCTTGTCC | TCTTAATCTT | 1920
| CCTCTCCAGA | ATAATCACAC | TGCAGCAGAT | ATGTATCTTT | CTCCTGTAAG | ATCTCCAAAG | 1980
| AAAAAAGGTT | CAACTACGCG | TGTAAATTCT | ACTGCAAATG | CAGAGACACA | AGCAACCTCA | 2040
| GCCTTCCAGA | CCCAGAAGCC | ATTGAAATCT | ACCTCTCTTT | CACTGTTTTA | TAAAAAGTG | 2100
| TATCGGCTAG | CCTATCTCCG | GCTAAATACA | CTTTGTGAAC | GCCTTCTGTC | TGAGCACCCA | 2160
| GAATTAGAAC | ATATCATCTG | GACCCTTTTC | CAGCACACCC | TGCAGAATGA | GTATGAACTC | 2220
| ATGAGAGACA | GGCATTTGGA | CCAAATTATG | ATGTGTTCCA | TGTATGGCAT | ATGCAAAGTG | 2280
| AAGAATATAG | ACCTTAAATT | CAAAATCATT | GTAACAGCAT | ACAAGGATCT | TCCTCATGCT | 2340
| GTTCAGGAGA | CATTCAAACG | TGTTTTGATC | AAAGAAGAGG | AGTATGATTC | TATTATAGTA | 2400
| TTCTATAACT | CGGTCTTCAT | GCAGAGACTG | AAAACAAATA | TTTTGCAGTA | TGCTTCCACC | 2460
| AGGCCCCCTA | CCTTGTCACC | AATACCTCAC | ATTCCTCGAA | GCCCTTACAA | GTTCCTAGT | 2520
| TCACCCTTAC | GGATTCCTGG | AGGGAACATC | TATATTTCAC | CCCTGAAGAG | TCCATATAAA | 2580
| ATTTCAGAAG | GTCTGCCAAC | ACCAACAAAA | ATGACTCCAA | GATCAAGAAT | CTTAGTATCA | 2640
| ATGGTGAAT | CATTCGGGAC | TTCTGAGAAG | TTCCAGAAAA | TAAATCAGAT | GGTATGTAAC | 2700
| AGCGACCGTG | TGCTCAAAAG | AAGTGCTGAA | GGAAGCAACC | CTCCTAAACC | ACTGAAAAAA | 2760
| CTACGCTTTG | ATATTGAAGG | ATCAGATGAA | GCAGATGGAA | GTAAACATCT | CCCAGGAGAG | 2820
| TCCAAATTTC | AGCAGAAACT | GGCAGAAATG | ACTTCTACTC | GAACACGAAT | GCAAAAGCAG | 2880
| AAAATGAATG | ATAGCATGGA | TACCTCAAAC | AAGGAAGAGA | AATGAGGATC | TCAGGACCTT | 2940
| GGTGGACACT | GTGTACACCT | CTGGATTCAT | TGTCTCTCAC | AGATGTGACT | GTAT | 2994